US00PP22741P2

(12) United States Plant Patent
Bradford

(10) Patent No.: US PP22,741 P2
(45) Date of Patent: May 22, 2012

(54) NECTARINE TREE NAMED 'FIRE TIME'

(50) Latin Name: *Prunus persica*
Varietal Denomination: Fire Time

(76) Inventor: Lowell Glen Bradford, Le Grand, CA (US)

( * ) Notice: Subject to any disclaimer, the term of this patent is extended or adjusted under 35 U.S.C. 154(b) by 8 days.

(21) Appl. No.: 12/928,445

(22) Filed: Dec. 13, 2010

(51) Int. Cl.
*A01H 5/00* (2006.01)

(52) U.S. Cl. ..... Plt./190

(58) Field of Classification Search ..... Plt./190
See application file for complete search history.

(56) References Cited

U.S. PATENT DOCUMENTS

| | | | |
|---|---|---|---|
| PP7,506 | P | 4/1991 | Bradford |
| PP10,888 | P | 5/1999 | Bradford |
| PP16,494 | P2 | 5/2006 | Bradford |

*Primary Examiner* — Susan McCormick Ewoldt

(57) ABSTRACT

The present invention relates to a new and distinct variety of nectarine tree, *Prunus persica*, broadly characterized by a small size, moderately vigorous, hardy, self-fertile, very productive and regular bearing tree. The variety blooms during the mid to late season and requires about 650 chilling hours. The fruit matures under the ecological conditions described in the beginning of August, with first picking on Aug. 1, 2010. The fruit is uniformly large in size, acidic and sweet in flavor, globose to slightly oblong in shape, clingstone in type, firm and melting in texture, mostly red in skin color, and yellow in flesh color.

1 Drawing Sheet

Botanical classification: *Prunus persica.*
Variety denomination: 'FIRE TIME'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'FIRE TIME'.

The present variety was hybridized by me in 2004 as a first generation cross using 'Western Pride' (U.S. Plant Pat. No. 10,888) nectarine as the selected seed parent and 'Grand Bright' (U.S. Plant Pat. No. 16,494) nectarine as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2007 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Western Pride' nectarine, by producing nectarines that are firm, large in size, and acidic in flavor, but is distinguished therefrom by producing fruit that is clingstone instead of freestone, that has a higher degree of red skin color, and that matures about one week later.

The present variety is similar to its pollen parent, 'Grand Bright' nectarine, by producing nectarines that are nearly full red in skin color, clingstone in type, firm in texture, and acidic in flavor, but is distinguished therefrom by producing fruit that matures about three weeks later.

The present variety is most similar to 'Summer Fire' (U.S. Plant Pat. No. 7,506) nectarine by producing nectarines that are nearly full red in skin color, clingstone in type, acidic in flavor, and large in size, but is distinguished therefrom by having a large instead of small blossom, by being more productive, and by producing fruit that matures about 5 days later.

SUMMARY OF VARIETY

In summary, the present nectarine variety is characterized by a small size, moderately vigorous, hardy, self-fertile, very productive and regular bearing tree. The variety blooms during the mid to late season and requires about 650 chilling hours. The fruit matures under the ecological conditions described in the beginning of August, with first picking on Aug. 1, 2010. The fruit is uniformly large in size, acidic and sweet in flavor, globose to slightly oblong in shape, clingstone in type, firm and melting in texture, mostly red in skin color, and yellow in flesh color.

DRAWING

The accompanying photograph consists of four whole fruits positioned to display the characteristics of the skin color and form, two sliced fruits to reveal the flesh, two insets to reveal buds and a blossom, and characteristic leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Aug. 7, 2010, on the original tree during its sixth growing season. The blossom and flower descriptions were made the previous blooming season. All major color code designations are by reference to the Inter-Society Color Council, National Bureau of Standards. Common color names are also used occasionally.

It is to be noted that the climatic conditions in 2010 led to delayed fruit ripening for most of the season, up to ten days during the early season and five days during the late season. This should be taken into account when comparing to other variety descriptions made referencing different years. However, the relative blooming times and ripening times cited in this application are accurate for 2010, and should remain about the same in future years.

Parentage

Seed Parent: 'Western Pride' nectarine (U.S. Plant Pat. No. 10,888).

Pollen Parent: 'Grand Bright' nectarine (U.S. Plant Pat. No. 16,494).

Tree

Size: Medium, reaching and maintaining a height of 8' [2.44 m.] and a spread of 6' [1.83 m.] after six growing seasons utilizing typical dormant pruning.

Vigor: Moderate vigor, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Pruned to a central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-fertile.

Bearing: Consistent bearer with no alternate bearing yet observed.

Approximate chilling requirement: 650 hours.

Trunk:

- *Size*.—Medium, reaching a maximum diameter of 2¼" [57.2 mm.] after the sixth growing season.
- *Texture*.—Shaggy.
- *Bark color*.—A Moderate brown [58. m.Br] and Dark grayish brown [62. d.gy.Br] variegation with Light yellowish brown [76. l.yBr] crevices present.
- *Lenticels*.—Approximate Number Per Square Inch: 8. Color: Dark orange yellow [72. d.OY]. Average Size: 5/16" [7.9 mm.]. Shape: Eye-shaped, elongated.

Branches:

- *Size*.—Diameter of first side limb is ¾" [19.1 mm.] measured 12" from the central leader.
- *Texture*.—Fairly smooth on first and second year wood, increasing roughness with age.
- *Color*.—1st Year Wood Topside: Grayish red [19. gy.R]. 1st Year Wood Underside: Brilliant yellow green [116. brill.YG]. 2nd Year Wood: Strong brown [55. s.Br]. Older Wood: A Deep brown [56. deep Br] and Dark grayish yellowish brown [81. d.gy.yBr] variegation.
- *Lenticels*.—Number Per Square Inch: About 80 on second year wood. Color: Moderate orange yellow [71. m.OY]. Size: 1/32" [0.8 mm.] to 3/32" [2.4 mm]. Shape: Eye-shaped, elongated.

Leaves:

- *Size*.—Medium. Average Length: 5⅜" [136.5 mm.]. Average Width: 1 7/16" [36.5 mm.].
- *Arrangement*.—Alternate.
- *Thickness*.—Medium.
- *Form*.—Elliptical.
- *Apex*.—Acuminate.
- *Base*.—Acute with an average base angle of 80 degrees.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Vein color*.—Light yellow green [119. l.YG].
- *Petiole*.—Average Length: 7/16" [11.1 mm.]. Average Thickness: 1/16" [1.6 mm.]. Color: Brilliant yellow green [116. brill.YG].
- *Stipules*.—Number: Usually 2 per leaf, up to 6 per growing tip. Average Length: ¼" [6.4 mm.]. Color: Brilliant yellow green [116. brill.YG] becoming Deep yellowish brown [75. deep yBr] with age.
- *Glands*.—Number: Mostly 2 to 4 per leaf. Position: Mostly alternate, positioned near the intersection of the petiole and base of blade. Size: Small. Form: Appear as globose when young, but taking on a reniform shape with maturity. Color: Brilliant yellow green [116. brill.YG] becoming Dark yellowish brown [78. d.yBr] with age.
- *Leaf buds*.—Pointed, medium in size.

Flower buds:

- *Hardiness*.—Half-hardy, with respect to central California winters.
- *Diameter*.—Typically ⅜" [9.5 mm.] 1 week before bloom.
- *Length*.—Typically 11/16" [17.5 mm.] 1 week before bloom.
- *Form*.—Not appressed.
- *Surface*.—Pubescent.
- *Tip color*.—Light pink [4. l.Pk].

Flowers: Perfect, complete, perigynous, usually a single pistil, about thirty stamens, five sepal and petal locations alternately positioned.

- *Type*.—Showy, large.
- *Average flower diameter*.—2" [50.8 mm.].
- *Number of petals*.—Usually five, extra petal fragments are occasionally observed.
- *Petal shape*.—Circular to oval.
- *Petal margin*.—Entire, slightly wavy.
- *Average petal diameter*.—¾" [19.1 mm.].
- *Average petal length*.—¾" [19.1 mm.].
- *Petal apex*.—Rounded.
- *Petal base*.—Rounded to somewhat truncate.
- *Petal color*.—Mostly Pale purplish pink [252. p.pPk] on both sides with some Moderate purplish pink [250 m.pPk] coloration on some.
- *Anther color*.—Moderate reddish orange [37. m.rO] over a Light yellow [86. l.Y] center at bloom onset.

*Stigma color*.—Pale yellow green [121. p.YG].
*Sepal color*.—Dark purplish red [259. d.pR] on the outer surface.
*Sepal length*.—¼" [6.4 mm.].
*Sepal width*.—3/16" [4.8 mm.].
*Sepal apex*.—Rounded to elliptical to match the sepal length and width.
*Sepal margin*.—Fairly smooth.
*Average pistil length*.—13/16" [20.6 mm.].
*Average stamen length*.—11/16" [17.5].
*Fragrance*.—Moderate.
*Blooming period*.—Mid to late seasonal, four days after 'Grand Bright' (U.S. Plant Pat. No. 16,494) nectarine.
*Onset of bloom*.—One percent on Feb. 27, 2010.
*Date of full bloom*.—Mar. 8, 2010.
*Duration of bloom*.—One to two weeks, dependent on ambient temperature.
*Number per cluster*.—1 to 3 with single flowers most common.

Fruit

Maturity when described: Firm ripe, Aug. 7, 2010.
Date of first picking: Aug. 1, 2010.
Date of last picking: Aug. 10, 2010.
Size: Uniform, large.
*Average diameter axially*.—3⅛" [79.4 mm.].
*Average diameter across suture plane*.—3" [76.2 mm.].
*Average diameter across cheek plane*.—2 15/16" [74.6 mm.].
*Typical weight*.—9 ounces [255 grams].
Form: Uniform, globose to slightly asymmetrical.
*Longitudinal section form*.—Mostly oval.
*Axial view*.—Round.
Suture: A shallow groove inside the stem cavity, a shallow trough along the side, and a shallow groove toward the apex extending past the pistil point.
Ventral surface: Rounded, lipped throughout, slightly stronger toward the apex.
Lips: Somewhat unequal.
Cavity: Flaring, slightly elongated in the suture plane, suture showing on one side, Brilliant yellow [83. brill.Y] stem markings present.
*Depth*.—⅝" [15.9 mm.].
*Breadth*.—1⅛" [28.6 mm.].
Base: Rounded to truncate.
Apex: Rounded.
Pistil point: Apical, negligible in length, mostly depressed within the suture.
Stem: Medium.
*Average length*.—⅜" [9.5 mm.].
*Average width*.—3/16" [4.8 mm.].
Skin:
*Thickness*.—Medium.
*Surface*.—Smooth.
*Tenacity*.—Tenacious to flesh.
*Astringency*.—Slightly astringent.
*Tendency to crack*.—None observed in dry season.
*Color*.—Deep red [13. deep R] smoothly blending into a Deep reddish orange [36. deep rO] background with some Very deep red [14. v.deep R] mottling spots and Moderate orange yellow [71. m.OY] freckling stronger toward the apex.
Flesh:
*Color*.—Very yellow [82. v.Y] with some Deep red [13. deep R] streaking throughout.
*Surface of pit cavity*.—Covered with Strong red [12. s.R] broken fibers when twisted from stone.
*Amygdalin*.—Moderate.
*Juice*.—Abundant, rich.
*Texture*.—Firm, tough, melting.
*Fibers*.—Abundant, fine.
*Ripens*.—Fairly evenly, slightly earlier at the apex.
*Flavor*.—Acidic, strong nectarine flavor, typically 14 brix.
*Aroma*.—Slight.
*Eating quality*.—Very good.

Stone

Type: Clingstone.
Form: Oval.
Hilum: Narrow, oblong.
Base: Slightly oblique to round.
Apex: Rounded with a ⅛" [3.2 mm] sharp tip.
Sides: Equal.
Surface: Irregularly furrowed and ridged toward the apex, pitted from the middle to the base.
Ridges: Jagged.
External color: Moderate reddish brown [43. m.rBr].
Pit wall color when cracked: Moderate reddish brown [43. m.rBr].
Cavity surface color: Strong brown [55. s.Br].
Average pit wall thickness: ¼" [6.4 mm.]
Average width: 1¼" [31.8 mm.].
Average length: 1 11/16" [42.9 mm.].
Average breadth: ⅞" [22.2 mm.].
Tendency to split: Slight.
Kernel:
*Form*.—Oval.
*Skin color*.—Brilliant yellow [83. brill.Y] when first removed.
*Pellicle color*.—Grayish brown [61. gy.Br].
*Vein color*.—Light orange yellow [70. l.OY].
*Taste*.—Sweet.
*Viable*.—Yes.
*Average width*.—9/16" [14.3 mm.].
*Average length*.—13/16" [20.6 mm.].
*Amygdalin*.—Scant.

Use

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Summer Fire' (U.S. Plant Pat. No. 7,506) nectarine by producing nectarines that are nearly full red in skin color, clingstone in type, acidic in flavor, and large in size, but is distinguished therefrom by having a large instead of small blossom, by being more productive, and by producing fruit that matures about 5 days later.

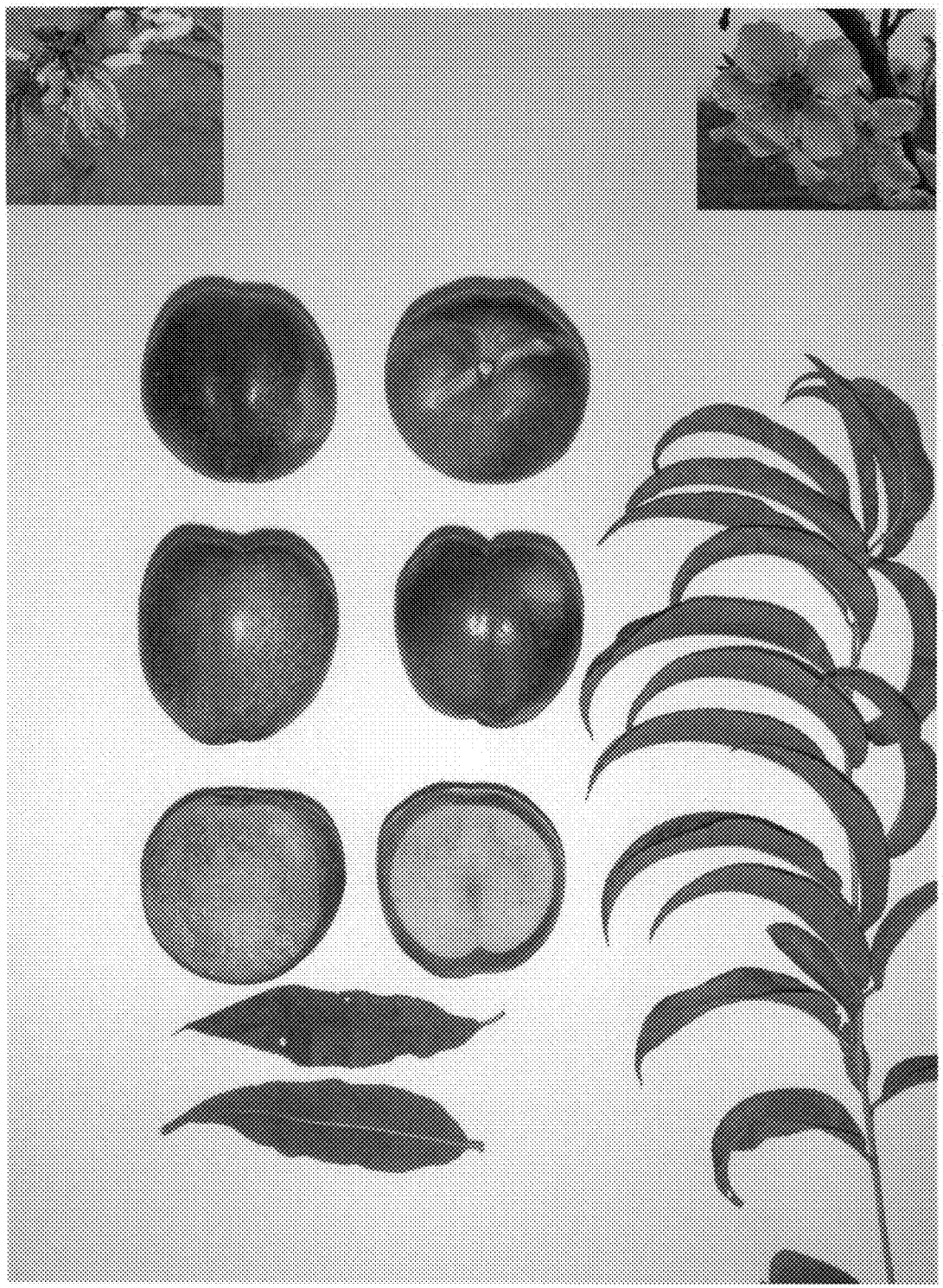

* * * * *